United States Patent [19]
Nusbaum

[11] Patent Number: 5,088,986
[45] Date of Patent: Feb. 18, 1992

[54] SAFETY SYRINGE

[76] Inventor: Michael J. Nusbaum, Livingston, N.J.

[21] Appl. No.: 619,460

[22] Filed: Nov. 29, 1990

[51] Int. Cl.⁵ ............................................. A61M 5/32
[52] U.S. Cl. .................................... 604/195; 604/198
[58] Field of Search .............. 604/187, 192, 195, 198, 604/263, 110

[56] References Cited

U.S. PATENT DOCUMENTS

| | | | |
|---|---|---|---|
| 4,795,432 | 1/1989 | Karczmer | 604/110 |
| 4,911,693 | 3/1990 | Paris | 604/198 X |
| 4,966,592 | 10/1990 | Burns et al. | 604/198 |
| 4,973,316 | 11/1990 | Dysarz | 604/195 |
| 4,994,034 | 2/1991 | Botich et al. | 604/110 |

Primary Examiner—John D. Yasko
Attorney, Agent, or Firm—Shlesinger, Arkwright & Garvey

[57] ABSTRACT

A safety device for use with a conventional hypodermic syringe including a needle shield for connection to the hypodermic syringe having a tubular housing slidably connected to a retractable needle sheath. The needle sheath is selectively lockable in a retracted position within the tubular housing so that a needle held by the hypodermic extension can be exposed for use. A handle can be used for retracting the needle sheath within the tubular housing to a locked position. A release tab is located on the exterior of the tubular housing for unlocking the needle from the retracted position, and allowing said needle sheath to automatically lock in the closed position.

12 Claims, 2 Drawing Sheets

1

SAFETY SYRINGE

FIELD OF THE INVENTION

This invention relates to safety syringes which prevent accidental contact with the needle point to prevent infection.

BACKGROUND OF THE INVENTION

Hypodermic syringes are commonly used by medical personnel to administer injections of medicinal fluids and to take blood samples or other fluid samples from the human body. The procedure generally involves penetration of the skin by a needle or similar device. In the typical situation, treatment of the injection area is necessary both before and after the hypodermic syringe is used. For example, a cotton swab dipped with a disinfectant, such as alcohol, is usually applied to the area where the injection is to occur. After the needle has been inserted beneath the skin and removed, it is usually necessary to cover the perforation with a gauze covering.

It is primarily before and after the injection that the needle is either held or set aside. If the needle is left exposed, a significant risk of accidental contact with the needle point by the medical practitioner exists.

In an effort to reduce the likelihood of accidental contact with the needle point, a variety of needle guards or shields have been developed to cover the needle after the injection and thereby protect the practitioner from accidental puncture by the needle. Generally the shield devices of the prior art require two hands in order to achieve operation of the sliding shield and do not have the ability of selectively locking the shield in the retracted position with the needle exposed.

FEATURES OF THE INVENTION

A primary feature of the disclosed invention is to provide a disposable hypodermic syringe and needle combination wherein the needle is protected to prevent accidental contact involving the needle before and after use.

It is another feature of the disclosed invention to provide a hypodermic syringe having a needle sheath which is retractable selectively to a locked or an unlocked position.

Still another feature of the disclosed invention is to provide a locking mechanism in a hypodermic syringe which will selectively prevent unsheathing the needle or lock the sheath in a retracted position with the needle exposed.

Yet another feature of the disclosed invention is to provide a quick release lever which will allow the needle sheath to spring back and lock in the closed position, thus encompassing the needle within the protecting sheath.

Still another feature of the invention is to prevent the undesirable sliding motion required by a manually operated sheath which requires one hand to slide the sheath back over the exposed needle and avoids the subsequent risk of accidental injection.

SUMMARY OF THE INVENTION

The safety syringe disclosed herein includes a needle guard assembly formed of a tubular member or housing which attaches about the exterior of the syringe body and includes a spring-biased needle sheath which is retractable within the tubular member. The needle sheath includes a disc mounted thereto and located within the tubular member. The disc includes a pair of lock engagement surfaces, the first lock engagement surface prevents the needle sheath from being retracted within the tubular member. Upon rotation of the disc, the lock engaging surface is moved away from the locking block and the needle sheath may be retracted. The needle sheath rides with the disc along the retraction path as the needle is exposed.

When fluid is being extracted from a container, it is not necessary that the needle sheath be retracted to the locked position. As the sheath is placed against the top of the container and pressed, the needle sheath retracts, but its biased against the top of the container by the interior spring. By not pressing the needle all of the way into the bottle, the disc does not ride beyond the second locking mechanism and the needle sheath will return to cover the needle as the needle is withdrawn from the bottle. As it returns, the rotational potential energy stored within the spring rotates the disk into the fully locked position. Thus locking is accomplished automatically.

When the injection is ready to be given, the handle is manually rotated into the unlocked position and then drawn back so that the needle is fully exposed and the needle sheath is locked in the retracted position with the disc locked behind the second lock engagement surface. After the injection has been given and the needle is withdrawn from the patient, the release tab is lifted in order to release the sheath which automatically springs forward to lock and enclose the needle thereby preventing further risk of contamination.

These and other features and advantages of the invention will be readily apparent in view of the following description and drawings of the above-identified invention.

DETAILED DESCRIPTION OF THE INVENTION

Figure 1:
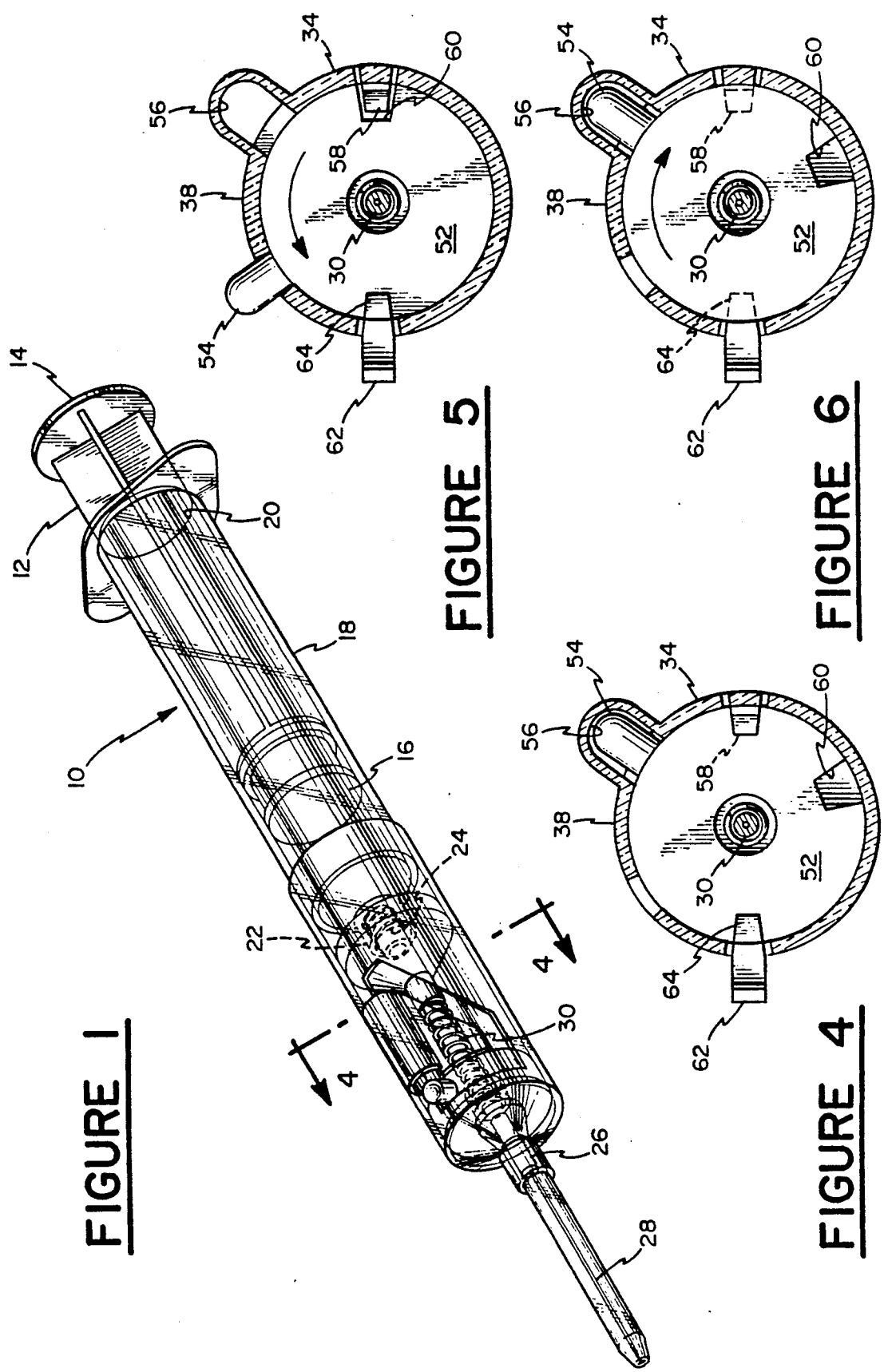
FIG. 1 is a perspective view of a syringe having the retractable and selectably lockable needle sheath.

As best shown in FIG. 1, the hypodermic syringe 10 of conventional design and material such as plastics includes a plunger 12 connected to a handle 14 and includes a fluid and air tight compressing end 16. Plunger 12 extends within fluid holding chamber 18 at the open end 20 and is movable from open end 20 to safety needle attachment end 22.

On the conventional hypodermic syringe 10, the needle attachment end 22 includes a threaded needle attachment portion 24 which is typically threaded for the industry standard needle attachment 26 at the base of needle 28.

In accordance with the present invention, a needle extension 30 is located between needle attachment end 22 and needle attachment 26. Needle extension 30 is threaded at one end and includes a generally rigid hollow fluid conduit for communicating fluid between needle 28 and fluid holding chamber 18.

The needle shield structure 32 of the present invention slides over the needle attachment end 22 of the fluid holding chamber 18 and is attached to the fluid holding chamber 18 at the threaded needle attachment end 24 by one end of needle extension 30.

The needle shield structure is preferably constructed of plastic material and will be further described with reference to FIGS. 2 and 3. The needle shield structure 32 includes an outer tubular member 34 being sized to slide over a portion of the fluid holding chamber 18 of the hypodermic syringe 10. A pentagonal opening 36 is formed in the side wall of the tubular member 34. A plate 38 is centrally located in the pentagonal opening to create a path or track 40 about the perimeter thereof. Plate 38 is held in position by a bridge 42 over the path 40. Tubular member 34 ends in a necked down sleeve 44 which surrounds the needle sheath 46.

Needle sheath 46 includes a needle exit opening 48 which is initially covered by a thin plastic membrane to insure sterility of the needle 28 prior to use. At the opposite end of needle sheath 46 is an enlarged seat 50 which is rigidly connected to actuating disc 52 which is located within the tubular member 34.

The operation and advantages of the actuating disc 52 are best shown in FIGS. 4–6, which is a cross-sectional view of the needle shield structure 32 taken along lines 4—4 of FIG. 1. FIGS. 4–6 are a sequence of the movement of the actuating disc 52 when first the needle is sheathed and locked, second when the needle is sheathed and unlocked, and third when the needle is unsheathed and the actuating member is in the locked position. In FIG. 1, the actuating disc 52 is shown in the sheathed and locked position which corresponds to the positioning in FIGS. 1 and 2. In FIG. 4, the manually operable handle 54 is aligned with bridge opening 56 beneath bridge 42. In this position, actuating disc 52 is prevented from sliding along needle extension 30 by block 58 which extends inwardly from tubular member 34. To unlock the actuating disc, handle 54 is rotated and slid along path 40 in a direction transverse to the needle 28. The path 40 is designated by the arrow in FIG. 3. When handle 54 is fully rotated as shown in FIG. 5, slot 60 in actuating disc 52 becomes aligned with block 58.

Figure 3:
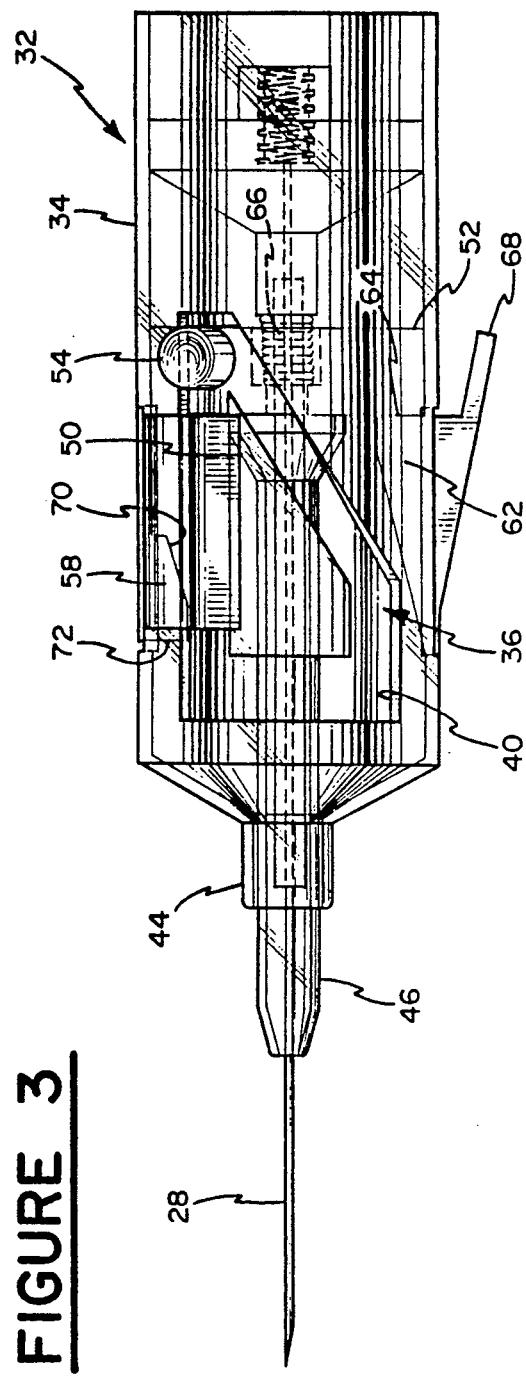

As the needle is unsheathed as shown in FIG. 3, the actuating disc 52 slides up path 40 and rotates to the position shown in FIGS. 3 and 6. As actuating disc 52 is slid along path 40 which can be accomplished by finger pressure, actuating disc 52 rides over biased block 62 and forces biased block 62 to protrude outwardly from tubular member 34. When actuating disc 52 is completely beyond block 62, then block 62 biases back into the normal position within tubular member 34 and actuating disc 52 is prevented from returning to the original position by the face 64 of block 62 which engages actuating disc 52.

Figure 2:
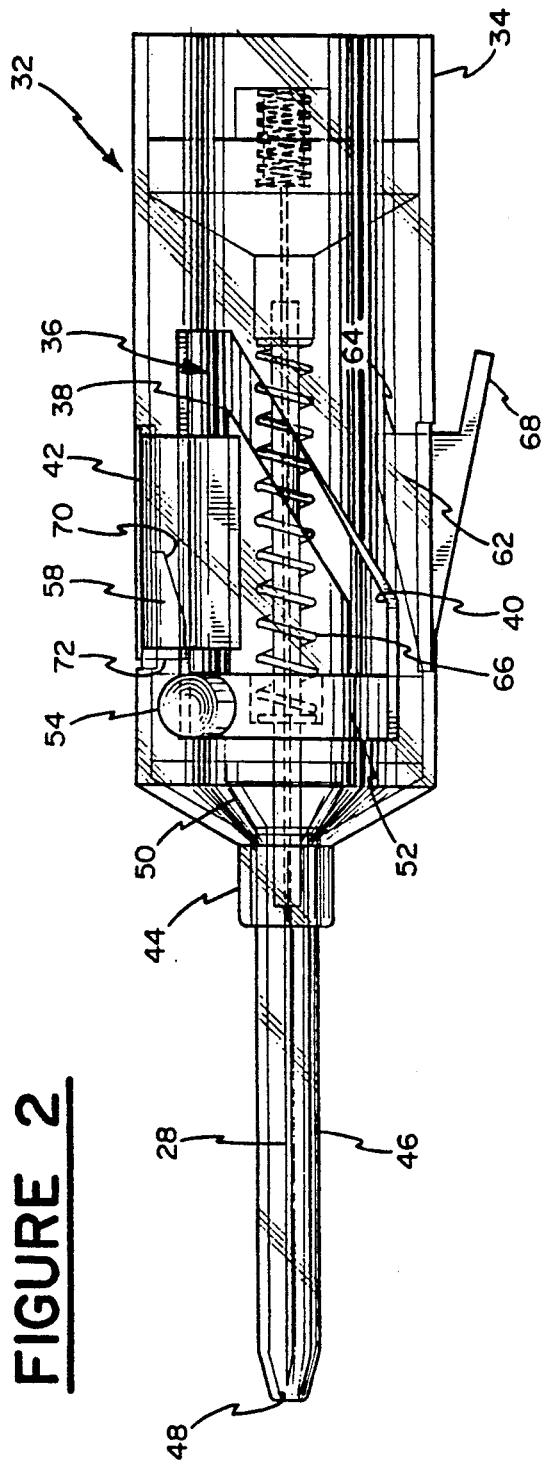
FIGS. 2 and 3 show the needle sheath wherein the needle is sheathed and unsheathed respectively; and, FIGS. 4, 5 and 6 are cross-sections taken along line 4—4 of FIG. 1 showing the locked and closed, unlocked and unclosed and retracted locked positions.

As shown in FIG. 2, spring 66 normally biases actuating disc 52 forward in the sheathed locked position. When actuating disc 52 is rotated, additional potential energy is stored in the spring. When the disk is moved to the unsheathed position, spring 66 is compressed and exerts a biasing force to push actuating disc 52 into the sheathed position as shown in FIGS. 1 and 2.

Block 62 includes release handle 68. When actuating disc 52 is in the unsheathed locked position shown in FIG. 3, release back to the sheathed and locked position can be simply accomplished by movement of release handle 68 outwardly from tubular member 34 whereupon spring 66 pushes actuating disc 52 into the locked and sheathed position. Pulling release handle 68 outwardly using a finger or thumb, from tubular member 34 causes face 64 to slide down along actuating disc 52 and disengage therefrom and manually operable handle 54 of actuating disk 52 snaps back along path 40 beneath bridge 42 and returns to the locked sheathed position.

As actuating member 52 moves along path 40 from the locked unsheathed position, to the locked sheathed position actuating member 52 slides along the inclined edge 70 of block 58 and pushes block 58 upwardly in a biased position as it goes by. After actuating disc 52 has passed by block 58, then block 58 snaps back down into place and the face 72 of block 58 prevents movement of the sheath 46 and actuating member 52.

It should be observed that the selectable locking feature of the invention occurs by the action of the spring 66. If the disc 52 is not moved rearwardly far enough, locking of disc 52 behind face 64 of biased block 62 does not occur, and upon release, spring 66 will force disc handle 54 back along path 40 in reverse direction. When it reaches the distal most part of the path, the stored rotational energy of the spring will force handle 54 back into the sheathed-locked position. This situation is most likely to occur during insertion of the needle 28 into a container. Upon withdrawal of the needle from the container, sheath 46 will cover the needle as it is withdrawn, and rotate back into the locked position. Therefore, during filling of the fluid holding container of the syringe body, the needle is never exposed and accidental injection is completely avoided.

While this invention has been described as having preferred design, it is understood that it is capable of further modification, uses and/or adaptations of the invention and including such departures from the present disclosure as come within known or customary practice in the art to which the invention pertains, and as may be applied to the essential features set forth, and fall within the scope of the invention or the limits of the appended claims.

I claim:

1. A safety device for preventing accidental contact with a hypodermic needle, said device comprising:
    a) needle shield means connectable to a syringe in a surrounding relationship to the needle;
    b) said needle shield means having an outer tubular member and a retractable needle sheath;
    c) said needle sheath being retractable within said tubular member to expose the needle;
    d) means for selectively releasably locking said sheath in the retracted position; and,
    e) whereby, the needle sheath may be retracted without being locked in the retracted position;
    f) said tubular member has a slot therein forming a track;
    g) a needle sheath retraction means having a handle slidably positioned in said track; and,
    h) said track is shaped so that said handle is movable in a continuous path about a perimeter of a section of the tubular member to return to the original starting position.

2. The safety device as defined in claim 1, further comprising:
    a) said means for locking said sheath in the retracted position having a pivotable release means thereon.

3. The safety device as defined in claim 2, wherein:
    a) said pivotable release means forms a tab extending outwardly of the said tubular member.

4. The safety syringe as defined in claim 1, wherein:
   a) said needle sheath retraction means includes a disc positioned within said tubular member, slidably positioned about a needle extension means; and,
   b) said disc is fixedly connected to said needle sheath.

5. The safety syringe as defined in claim 4, wherein:
   a) a spring is positioned about said needle extension means to bias said needle sheath in position covering the needle.

6. A safety device for use with a hypodermic syringe, said device comprising:
   a) needle shield means for connection to the hypodermic syringe;
   b) said needle shield means including a tubular housing slidably connected to a retractable needle sheath;
   c) said retractable needle sheath being selectively lockable in a retracted position so that a needle held by the hypodermic syringe can be exposed for use;
   d) means for retracting said needle sheath within said needle sheath means to a locked position; and,
   e) means for unlocking said needle sheath from said locked position;
   f) a handle connected to said needle sheath and extending through said tubular housing for manually retracting said sheath;
   g) said handle moves in a path formed in said tubular housing; and,
   h) said path formed in said tubular housing forms a closed loop.

7. The safety device of claim 6, further comprising:
   a) means for biasing said needle sheath in a position extending from said tubular housing.

8. The safety device of claim 6, wherein:
   a) said needle shield means includes a needle extension means for connection between the hypodermic syringe and a needle.

9. The safety device of claim 6, wherein:
   a) said loop forms a pentagonal shape.

10. The safety device of claim 6, wherein:
    a) said handle is moveable in at least one direction about said loop during locking and unlocking of said needle sheath in the retracted position.

11. The safety device of claim 6, wherein:
    a) a plate is positioned centrally of said loop and is held in place by a bridge extending over said path.

12. The safety device of claim 5, wherein:
    a) said spring includes a first end and a second end;
    b) said first end is fixedly connected to said disk;
    c) said second end is fixedly connected to said needle extension means;
    d) said spring being pre-rotated to produce a torque on said disk so that said disk is predisposed to rotate toward the locked position.

* * * * *